US 9,566,211 B2

(12) United States Patent
Brunner et al.

(10) Patent No.: US 9,566,211 B2
(45) Date of Patent: Feb. 14, 2017

(54) METHOD AND DEVICE FOR GENERATING A NANOAEROSOL

(75) Inventors: Peter Brunner, Ismaning (DE); Hans Peter Zarfl, Wolfsberg (AT); Bernd Heiko Lindena, Gruenwald (DE)

(73) Assignee: Medic Activ Vertriebs GmbH, Gruenwald (DE)

( * ) Notice: Subject to any disclaimer, the term of this patent is extended or adjusted under 35 U.S.C. 154(b) by 1219 days.

(21) Appl. No.: 13/521,419

(22) PCT Filed: Jun. 17, 2010

(86) PCT No.: PCT/EP2010/058586
§ 371 (c)(1),
(2), (4) Date: Nov. 28, 2012

(87) PCT Pub. No.: WO2011/082838
PCT Pub. Date: Jul. 14, 2011

(65) Prior Publication Data
US 2013/0067656 A1    Mar. 21, 2013

(30) Foreign Application Priority Data
Jan. 10, 2010  (EP) .................................... 10150393

(51) Int. Cl.
*A61H 33/06*  (2006.01)
*A61M 11/00*  (2006.01)
(Continued)

(52) U.S. Cl.
CPC .............. *A61H 33/06* (2013.01); *A61H 33/14* (2013.01); *A61H 35/00* (2013.01); *A61M 11/00* (2013.01);
(Continued)

(58) Field of Classification Search
CPC ..... A61M 11/002; A61M 15/00; A61H 33/06; B05B 7/30
See application file for complete search history.

(56) References Cited

U.S. PATENT DOCUMENTS 4,588,129 A * 5/1986 Shanks ................. B05B 7/0012
128/200.18
4,746,067 A * 5/1988 Svoboda ................ A61M 11/06
128/200.18
(Continued)

FOREIGN PATENT DOCUMENTS

EP     1 806 157 A2    7/2007
WO       0044331 A1    8/2000
WO    2009087053 A1    7/2009

*Primary Examiner* — Ryan Reis
(74) *Attorney, Agent, or Firm* — Robert A. Blaha; Smith Tempel Blaha LLC

(57) ABSTRACT

The invention relates to a method and a device for generating a nanoaerosol, wherein at least one fluid to be atomized is atomized in a nozzle via a nozzle opening of the nozzle along a discharge direction in the form of fluid particles, the atomized fluid particles are deflected from the discharge direction and larger fluid particles are at least partially separated from smaller fluid particles, the separated larger fluid particles are returned to the fluid to be atomized and the smaller fluid particles are dispensed onto the environment. A cartridge in which the nozzle and the fluid to be atomized are arranged is used. According to the invention, a stream of a carrier gas is generated in the nozzle and at least one fluid to be atomized is brought into contact with the carrier gas.

20 Claims, 4 Drawing Sheets

(51) Int. Cl.
  *A61H 35/00* (2006.01)
  *A61M 35/00* (2006.01)
  *B05B 1/26* (2006.01)
  *B05B 5/03* (2006.01)
  *B05B 7/00* (2006.01)
  *B05B 7/24* (2006.01)
  *A61H 33/12* (2006.01)
  *A61H 33/14* (2006.01)
  *A61M 11/02* (2006.01)
  *A61M 11/06* (2006.01)
  *A61M 15/00* (2006.01)

(52) U.S. Cl.
  CPC ........ *A61M 11/002* (2014.02); *A61M 15/0036* (2014.02); *A61M 35/00* (2013.01); *B05B 1/267* (2013.01); *B05B 5/03* (2013.01); *B05B 7/0012* (2013.01); *B05B 7/2424* (2013.01); *A61H 33/12* (2013.01); *A61H 2033/068* (2013.01); *A61H 2033/141* (2013.01); *A61M 11/02* (2013.01); *A61M 11/06* (2013.01); *A61M 15/0028* (2013.01)

(56) References Cited

U.S. PATENT DOCUMENTS

| | | | | |
|---|---|---|---|---|
| 5,235,969 | A * | 8/1993 | Bellm | B05B 7/0012 128/200.18 |
| 5,579,757 | A * | 12/1996 | McMahon | A61M 11/06 128/200.14 |
| 6,612,303 | B1 * | 9/2003 | Grychowski | A61M 11/06 128/200.14 |
| 7,992,803 | B2 * | 8/2011 | Mahoney | B05B 7/0012 239/318 |
| 2007/0074722 | A1 * | 4/2007 | Giroux | A61M 11/06 128/203.15 |
| 2007/0107725 | A1 | 5/2007 | Addington et al. | |
| 2009/0234269 | A1 | 9/2009 | Tavger | |

* cited by examiner

METHOD AND DEVICE FOR GENERATING A NANOAEROSOL

TECHNICAL FIELD

The present invention relates to a method and to a device for generating a nanoaerosol by atomizing fluids, in particular to a method and to a device for generating a nanoaerosol, especially a nanoaerosol for therapeutic, diagnostic or disinfection purposes.

BACKGROUND

It is well known that liquid disinfection agents can be sprayed as finely divided droplets, for example to disinfect items or air of a room contaminated with harmful aerosols. In addition, the beneficial effects of vapors or aerosol mists consisting of finely divided water or oil droplets have also long been known. In conventional sauna or steam baths, water or an aqueous emulsion containing a small amount of essential oils is evaporated. The hot steam cools down in the sauna cabinet and condenses to form mist droplets. A disadvantage of generating mist by evaporating water or an aqueous oil emulsion lies in the high temperature of the generated mist. While the stimulating effect of the hot mist can be vital for certain applications, conventional sauna and steam baths still suffer from the disadvantage that the circulation of the bather is severely challenged, and thus saunas and steam baths are contra-indicated for many groups of people. Thus, it has been suggested that aqueous solutions or emulsions be atomized at lower temperatures, typically at temperatures below 35° C. or 40° C., preferably at temperatures in a temperature range of 22-28° C. The stress on the circulation of the person to be treated would be reduced compared with conventional sauna or steam baths.

In the international patent application WO 00/44331 A1 a whole body mist bath device and a method for administering a whole body mist bath are described, wherein a mist bath is generated at temperatures below 35° C. To this end, a liquid is compressed to a pressure of more than 100 bar and then expelled through a nozzle in an explosive manner into a treatment cabinet so that on being expelled into the cabinet, the liquid is atomized into many small droplets of liquid due to its high internal pressure. In WO 00/4433 A1 it has already been proposed that aqueous salt solutions or oils with vitamin supplements or essential additives could be used to generate a mist. If a mist is to be produced from two different liquids, according to WO 00/44331, two separate nebulizers are used. In the nebulizers described in that document, a compression volume in the form of a hollow cylinder with a closable opening is provided which is connected via a line to a high pressure pump which delivers the liquid to be nebulized.

In the international patent application WO 2009/087053 A1 a method and a device for atomizing fluids is described, in particular for generating a therapeutically effective aerosol in a treatment area, wherein an aerosol generator is used which pressurizes the fluid to be atomized and which expels it at a flow rate in the range 50-300 m/s through at least one discharge opening in the form of small particles into a treatment area. In one embodiment of the device described in WO 2009/087053, the fluid to be atomized is disposed in a cartridge that comprises at least one discharge opening for atomizing fluid and a movable piston that can be moved by means of a drive means. The movable piston exerts a pressure on the fluid in the cartridge such that the fluid is dispensed through the discharge opening at the required flow rate of 50-300 m/s in the form of a finely divided mist of liquid.

One of the disadvantages of the known devices described above, however, is that the particles of liquid are generated with a relatively broad size distribution. Typically, the aerosol mist contains a mixture of particles with a diameter from a few nanometers to several micrometers. However, many applications for aerosols require and desire particle sizes in the sub-micrometer range. If in such cases particles are also dispensed with larger diameters, this results in an unnecessary loss of fluid that is not effectively put to use, which is a particular disadvantage when the fluid contains an active substance.

SUMMARY

Hence, the technical problem underlying the present invention is to provide a method and a device for generating a nanoaerosol wherein fluid particles essentially with a particle diameter of less than 1000 nanometers are produced. The corresponding device in this case should be simple and cheap to manufacture and operate, and in particular be able to atomize fluids containing active substances in a sterile manner.

This technical problem is solved by the cartridge for generating a nanoaerosol and an aerosol generator in accordance with the independent claims. Further advantageous embodiments are defined by the subject matter of the dependent claims.

Thus, the invention relates to a method for generating a nanoaerosol, wherein at least one fluid to be atomized is atomized in a nozzle via a nozzle opening of the nozzle along a discharge direction in the form of fluid particles, the atomized fluid particles are deflected from the original discharge direction, and larger fluid particles are at least partially separated from smaller fluid particles, and the separated larger fluid particles are returned to the fluid to be atomized, and the smaller fluid particles are dispensed onto the environment. The concept behind the invention is that atomization of a fluid by expelling the fluid from a nozzle necessarily produces fluid particles with a relatively broad distribution of sizes. Instead of dispensing the generated fluid particles directly into the environment, it is proposed that the atomized fluid particles be initially deflected out of the discharge direction so that the larger fluid particles can be separated from the smaller fluid particles. In the method according to the invention, the fluid particles which are eventually dispensed into the environment have a greatly reduced proportion of larger particles, and preferably essentially only smaller fluid particles. Thus, the method of the invention can be used to generate smaller fluid particles in a desired size range, while larger fluid particles are returned to the fluid to be atomized so that loss of fluid to be atomized by dispensing fluid particles in an unwanted size range can be avoided and the fluid to be atomized can be atomized essentially entirely in the form of fluid particles in the desired size range. The desired size range for the dispensed small fluid particles can in particular be adjusted and optimized by modifying the rheological properties of the fluid to be atomized and the operating parameters and the geometry of the atomizing device.

In the method according to the invention, a cartridge is preferably employed in which the nozzle and the fluid to be atomized are disposed. The cartridge, which will be described below in more detail, may be a reusable cartridge; particularly preferably, it is a disposable cartridge.

The fluid can be expelled from the nozzle in various manners. As an example, a movable piston may be provided which forces the fluid to the nozzle opening. In contrast to the cartridge described in WO 2009/087053 A1, for example, in this case the piston would not expel all of the fluid in a single stroke, since in the context of the present invention, larger fluid particles are returned to the fluid to be atomized. Rather, each stroke would only expel a portion of the fluid so that a piston operating periodically over several cycles would atomize all of the fluid to be atomized including the larger particles returned during each cycle. However, such a variant is not very effective having regard to the separation of larger and smaller fluid particles, since in the absence of further measures, the smaller fluid particles would be dispensed into the environment passively by diffusion. In addition, a mechanically actuated piston is a common source of faults when operating the device.

In a particularly preferred variant, a movable piston is not used and a stream of a carrier gas is generated in the nozzle and brings the at least one fluid to be atomized into contact with the carrier gas. The fluid is thus driven out of the nozzle by means of the carrier gas and atomized into fluid particles. The carrier gas also acts to dispense the smaller fluid particles into the environment.

The nozzle is thus preferably constructed such that the fluid to be atomized is drawn up and atomized by means of an underpressure generated in the nozzle. This underpressure can be generated by the carrier gas flowing out of the nozzle in an application of the known Venturi principle.

Particularly preferably, a hermetically sealed cartridge is used, so that the method of the invention is particularly suited to dispensing sterile fluids which contain active substances and are stored in the cartridge. Prior to use, openings are made in the cartridge to allow the carrier gas to be fed in and the atomized smaller fluid particles to be dispensed into the environment. Depending on the purpose and the fluid used, however, sealable or open cartridges may be used, which means that, for example, they can be refilled while in operation; this may be advantageous when a lot of fluid is used, for example when disinfecting air.

In accordance with a particularly simple embodiment of the method according to the invention, the larger fluid particles are returned to the fluid to be atomized under gravity, while the smaller fluid particles are dispensed into the environment in a direction that differs from the direction of gravitational pull, for example vertically upwards. In this regard, for example, discharge openings may be provided in the upper region of the cartridge from which the carrier gas can escape, entraining the smaller fluid particles.

The fluid to be atomized preferably comprises at least one active substance. The active substance can, for example, be selected from the group formed by active substances consisting of disinfecting agents, deodorizing agents, fragrances, cosmetics and diagnostic and/or therapeutic agents for the treatment of living beings. Examples of typical active substances are pharmaceuticals, hyaluronans, vitamins, acidifying agents or vegetable or synthetic oils. Furthermore, substances that modify the immune system, for example with paramunity-inducing substances, may also be used as active substances. Examples of substances suitable for disinfecting the air are oxidative substances such as percarbonic acid. The fluid to be atomized may be an aqueous solution, an aqueous emulsion, in particular an oil-in-water emulsion, an oily solution, an oily emulsion, in particular a water-in-oil emulsion, an aqueous suspension or an oily suspension. A particularly preferred aqueous solution is a salt solution. A particularly preferred oily solution is a solution which comprises essential oils. The fluid to be atomized may also comprise special active substance preparations typically in the form of negatively charged lipid vesicles with the active substance in the core of a lipid shell or in the lipid shell itself.

The therapeutically effective agents for the treatment of living beings, for example, in the case of the topical application of the generated nanoaerosol, may include drugs for the treatment of skin diseases or, in the case of inhalation of aerosol, may include drugs for treating diseases of the airways. Agents for the treatment of general illnesses and agents for enhancing well-being, for example substances familiar to the wellness industry, may also be used.

The atomized smaller particles which are dispensed into the environment may, for example, be dispensed onto the items to be treated with a stationary or portable device (for example in the case of a disinfection procedure). Particularly preferably, however, the atomized smaller particles are dispensed into a treatment area. The treatment area in this case may be any area that is suitable for the application in hand which, for example, can allow the skin or airway of a person to be treated or an animal to be treated to come into contact with the atomized nanoaerosol particles. In this respect, the treatment area may, for example, also be an inhalation mask. Preferably, however, the treatment area is a treatment chamber, which partially or completely surrounds the living being to be treated with the nanoaerosol.

In a preferred variant of the method of the invention, at least a portion of the smaller fluid particles to be dispensed are electrostatically charged. If the object or living being to be treated is earthed or is connected to an opposite potential, treatment can be particularly effective since in this case the smaller fluid particles to be dispensed are attracted by the object or living being to be treated.

In accordance with the invention, the smaller fluid particles have a diameter of less than 1000 nanometer, preferably a diameter of 5-750 nm, in particular 5-300 nm, and particularly preferably a diameter of 10-300 nm, in particular 10-200 nm. By matching the rheological properties of the fluid to be atomized, optimizing the nozzle and the pressure and/or the throughput of the carrier gas, the mean diameter of the smaller fluid particles that are delivered can be adjusted to a certain extent. Since the dispensed aerosol mist contains practically no fluid particles with a diameter of more than one micrometer, when used for inhalation purposes, for example, practically all of the particles generated gain ready access to the lungs. For disinfection applications, using a nanoaerosol means that no film of moisture is deposited on the objects to be disinfected, so that to a certain extent "dry" disinfection is made possible. Harmful agents present in suspended droplets can be attacked by collisions with the fluid particles generated in accordance with the invention resulting, for example, in a reduction in the pH or oxidation in the droplets containing the harmful agents.

The invention also relates to a cartridge for generating a nanoaerosol, having at least one reservoir for the fluid to be atomized, a demixing chamber which comprises a deflection device and at least one discharge opening for the fluid to be atomized, a nozzle which has at least one nozzle opening leading into the demixing chamber and at least one channel from the reservoir, which opens into the nozzle. The nozzle opening is preferably disposed on a longitudinal axis of the nozzle; the deflection device is disposed in the extension of the axis.

Preferably, there is a communicating connection between the reservoir and the demixing chamber so that a portion of the deflected fluid particles, in particular fluid particles with a larger diameter, can return from the demixing chamber to the reservoir.

As mentioned above, in a particularly preferred embodiment, the nozzle operates with a carrier gas. Thus, at least one supply line which opens into the nozzle is provided for a carrier gas.

In a variant of the cartridge of the invention, the supply line for the carrier gas is formed as a central bore which leads at one end into the base of the cartridge and its other end merges into the nozzle.

In order to form a hermetically sealed cartridge, the bore opening in the base of the cartridge is sealed by a pierceable wall. In this case, the at least one discharge opening for the fluid to be atomized is also preferably sealed by a pierceable or tear-open wall. As an example, one or more tear tabs may be disposed on the top of the cartridge by means of which openings can be formed in the top.

In a preferred variant of the cartridge of the invention, the nozzle is formed as a Venturi nozzle.

The cartridge may also comprise means for connecting the reservoir with an electrical voltage supply source. In a variant, in which the cartridge is exclusively formed from an electrically non-conductive material, for example from a non-conductive plastic material, these means may, for example, consist of a pierceable, initially sealed opening in the base of the cartridge through which, prior to using the cartridge, an electrode connected to the electrical voltage supply source is introduced into the cartridge in such a manner that the electrode comes into contact with the fluid to be atomized. In a further variant, the nozzle may consist at least in part of an electrically conductive material and means may be provided for connecting the nozzle with an electrical voltage supply source.

In accordance with a preferred embodiment, the cartridge consists of at least two components which can be connected together after filling with the fluid to be atomized. Connection of the two components may, for example, be by means of a plug and socket type connection, screw type connection or the like. Particularly preferably, the connection is constructed in such a manner that after filling with the fluid to be atomized, the two components are connected such that a user cannot disconnect them. As an example, the two components may be bonded or welded. In this case, the fluid to be atomized can be hermetically sealed in the cartridge so that until it is put to use, it is guaranteed that no contamination can enter the cartridge from outside, thereby ensuring that the fluid contained therein is sterile, for example.

In the cartridge sealed in this manner therefore the fluid to be atomized is contained.

Subject of the invention is also an aerosol generator comprising a mounting to accommodate at least one cartridge as hereinbefore described and means for expelling the fluid contained in the fluid in the form of a nanoaerosol.

Preferably, the means for expelling the fluid contained in the cartridge comprises a source of a carrier gas, wherein the mounting has at least one first hollow spike which communicates with the source of the carrier gas and can penetrate into the supply line for the carrier gas of the cartridge, and at least one second hollow spike which communicates with the environment and can penetrate into the discharge opening for the fluid of the cartridge to be atomized. Prior to expelling the fluid, the first hollow spike and the second hollow spike are mechanically, for example hydraulically or pneumatically, driven into the hermetically sealed cartridge. Instead of the second hollow spike for opening the discharge opening of the cartridge, the cartridge itself may be provided with appropriate tear tabs which are arranged such that on moving the cartridge in the mounting, one or more discharge openings are exposed. The tear tabs may, for example, be disposed on the top of the cartridge such that when the cartridge is moved in the mounting, they snap off and form one or more openings on the top of the cartridge which communicate with the demixing chamber of the cartridge.

The source of the carrier gas may, for example, be a compressor or a compressed gas bottle which preferably contains an inert gas.

In accordance with a further preferred embodiment, the aerosol generator also comprises an electrical voltage supply source which can be connected with the cartridge, for example in the form of an electrode that can be driven into the cartridge.

The invention also relates to a mist bath device with a bath or treatment area to accommodate at least one living being to be treated or parts of the body of a living being to be treated, wherein the mist bath device is characterized in that it comprises at least one aerosol generator of the type described above. The mist bath device may, for example, be an aerosol cabinet as described in international patent applications WO 00/44331 A1 and WO 2009/087053 A1.

Preferably, the mist bath device also comprises means for earthing the living being or parts of its body to be treated or to charge it electrostatically with the opposite sign to the liquid to be atomized. In addition, deposition of the charged nanoparticles on the body or parts of the body of the living being may be enhanced by means of an externally applied electromagnetic field.

Finally, the present invention relates to a use of the cartridge of the invention for the therapeutic treatment of living beings, wherein the nanoaerosol which is generated is taken up via the lungs, skin or in the form of a whole body inhalation.

Typical quantities of liquid atomized in the context of a treatment depend on the dimensions of the treatment area in which the aerosol mist is to be generated. When handling parts of a person's body, liquid quantities of a few milliliters are amply sufficient. When treating a person in a mist bath device accommodating the whole person, typically 1 to 25, preferably 1-20 ml of liquid is atomized, whereas when treating large animals, for example horses in appropriate stalls or cubicles, up to 100 ml of liquid per treatment can be atomized. The dimensions of the cartridge of the invention are each matched to the quantity of liquid to be atomized. Alternatively, the required quantity of liquid can be atomized by means of several cartridges either one after the other or simultaneously. The principle of the cartridge of the invention, however, does not limit it to a specific volume. Substantially larger volumes of fluid than those mentioned above are also possible. Thus, for example, when disinfecting the air of large areas over a long time period, for example an aircraft cabin during an intercontinental flight, much larger cartridges may be used. Variants may also be envisaged wherein the cartridge of the invention can be refilled or recharged. The cartridge may, for example, have a refilling opening or be connected via a refill line to a storage vessel for the fluid to be atomized.

BRIEF DESCRIPTION OF THE DRAWINGS

The invention will now be described in more detail with reference to the accompanying drawings. In the drawing.

DETAILED DESCRIPTION

Figure 1:
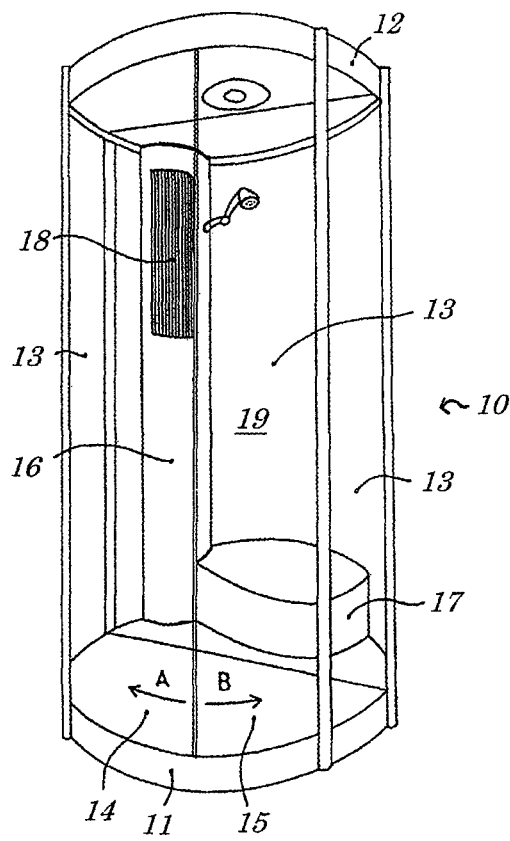
FIG. 1 shows a mist bath device suitable for carrying out the method according to the invention.

FIG. 1 shows a mist bath device with the general reference numeral 10 as has been described, for example, in international patent applications WO 00/44331 A1 and WO 2009/087053 A1. The mist bath device 10 is spatially defined by a base panel 11, a top panel 12, side screens 13 formed from acrylic glass and two front screens 14, 15 which are movable in the directions of arrows A, B and which provide access to the treatment chamber 10. A pipe 16 in the mist bath device 10 extends between the base panel 11 and the top panel 12. In addition, a waterproof bench seat 17 is disposed above the base panel 11. Instead of the means for generating an aerosol described in WO 00/44331 A1 and WO 2009/087053 A1, in the pipe 16 the mist bath device 10 has an aerosol generator in accordance with the invention which will be described in more detail below. The aerosol which is generated can flow via a grille 18 disposed in the pipe 16 into the treatment area 19.

If, as will be described below in more detail, the aerosol particles generated are electrostatically charged, the bench seat 17 can be earthed or oppositely charged. When the person to be treated sits on the bench seat, the aerosol particles in the treatment area 19 will be attracted by the person to be treated. Correspondingly, for example, the side walls 13 of the mist bath device 10 may, for example, be formed from a conductive material which, after the treatment is completed, is oppositely charged to the aerosol particles. The rest of the aerosol particles in the treatment area are then attracted to the side walls and can then be readily wiped away. Alternatively or in addition, a blower (not shown in FIG. 1) may be provided which draws the remaining aerosol particles from the treatment area 19 after the treatment. This ensures that even the sub-micrometer aerosols produced with the aerosol generator of the invention can be effectively removed from the treatment area 19 before the mist bath device is used again.

Figure 2:
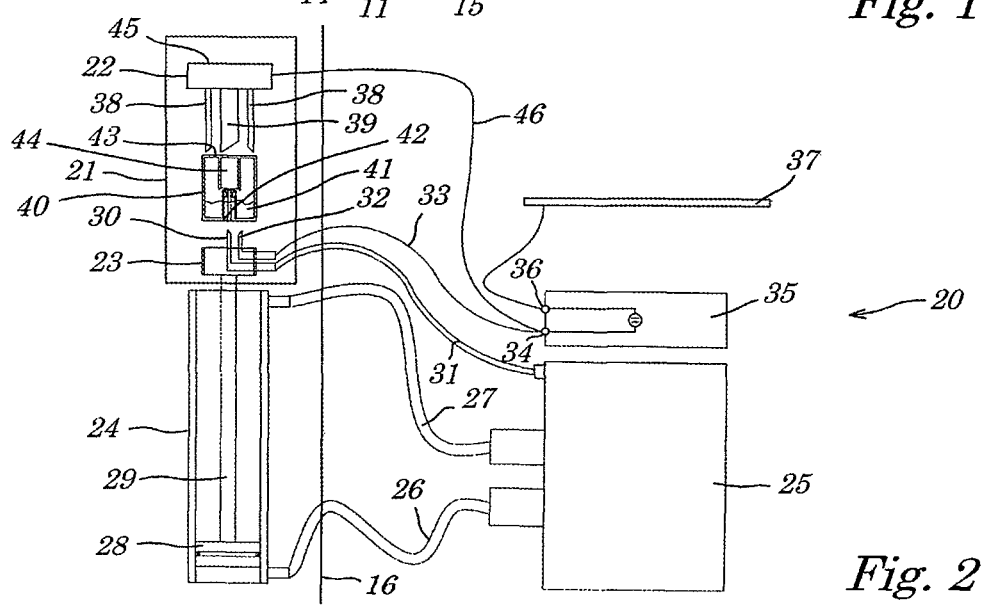
FIG. 2 shows a schematic diagram of the principle of one embodiment of the aerosol generator according to the invention.

FIG. 2 diagrammatically shows an aerosol generator according to the invention, with general reference numeral 20, which may be used in the mist bath device 10 of FIG. 1. The aerosol generator 20 has a mounting 21 for an exchangeable cartridge which contains the fluid to be atomized. In the example shown, the mounting 21 has a fixed upper part 22 and a movable lower part 23, which is connected to a pneumatic drive 24. The mounting 21 and the pneumatic drive 24 may, for example, be disposed in the pipe 16 of the mist bath device 10 of FIG. 1. The pneumatic drive 24 is connected to a compressor 25 which, for example, may be disposed under the bench seat 17 of the mist bath device 10. Two compressed air lines 26, 27 are pressurized alternately and lead from the compressor to the pneumatic drive in order to move the piston 28 to and fro. The piston 28 is connected with the movable lower part 23 of the mounting 21 via a piston shaft 29. A central hollow spike 30 is disposed in the mounting 23 and is also connected to the compressor 25, via a line 31, and can be pressurized with compressed air. Further, in the movable lower part 23 of the mounting 21, a metal tip 32 is disposed which is connected via an electrical cable 33 with one pole 34 of a low current supply 35. The other pole 36 of the low current supply 35 may, for example, be connected with a metal plate 37 set into the seat 17 of the mist bath device 10 of FIG. 1. In the embodiment shown, the fixed upper part 22 of the mounting 21 has a central guide spike 38 and hollow spikes 39 disposed in a circle around the guide spike 38.

An initially hermetically sealed cartridge 40, which will be described in more detail in connection with FIGS. 3-13, is inserted in the mounting 21. Fluid 41 to be atomized is in the cartridge 40. The pneumatic drive 24 compresses the cartridge 40 between the upper part 22 and the lower part 23 of the mounting 21 such that the hollow spike 30 and the metal tip 32 can penetrate the base 42 of the cartridge 40, while the spikes 39 pierce the top 43 of the cartridge. The guide spike 38 in this case penetrates into a depression 44 provided in the top of the cartridge 40. In order to generate the nanoaerosol, compressed air is blown into the cartridge 40 via the hollow spike 30. The compressed air and smaller aerosol particles in the sub-micrometer range leave the cartridge 40 via the hollow spikes 39 and enter the environment from the top 45 of the upper part 22 of the mounting 21. In order to prevent deposition of aerosol particles on the upper part 22 of the mounting 21, the upper part 22 can be connected to the same pole 34 of the electrical supply 35 which is also connected to the metal tip 32 which acts as an electrode so that the upper part 22 and the aerosol particles generated develop the same charge.

Figure 3:
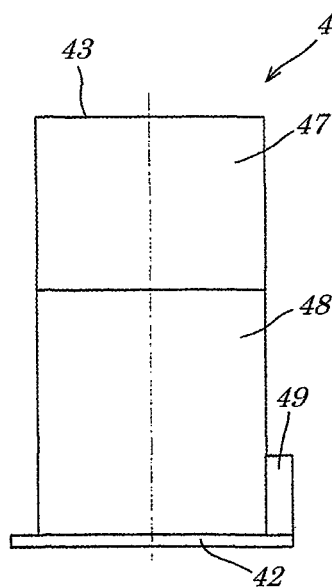
FIG. 3 shows a preferred embodiment of the cartridge of the invention in side view.

FIG. 3 is a first variant of the cartridge 40 according to the invention in a diagrammatic side view. The outer housing of the cartridge 40 consists of two injection molded parts 47, 48 which can be connected together after filling with the fluid to be atomized in a manner, for example by bonding or ultrasound welding, such that a user cannot separate them. In the sealed condition shown in FIG. 3, the fluid to be atomized is hermetically sealed in the cartridge 40. The lower part 48 of the cartridge 40 has a protruding lug 49 to assist in correctly inserting the cartridge in the mounting 21 of the aerosol generator of FIG. 2. In the example shown, the cartridge is approximately 55 mm high, with a diameter of approximately 30 mm. Several milliliters of a fluid can be dispensed into the mist bath device of FIG. 1 using such a cartridge.

Figure 4:
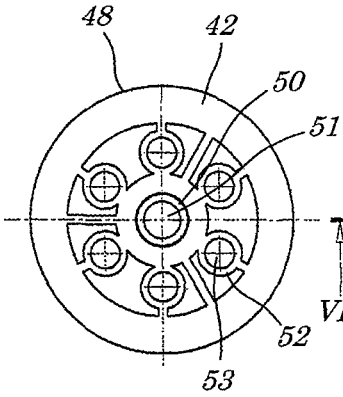
FIG. 4 shows a base view of the cartridge of FIG. 3.

FIG. 4 shows the base 42 of the cartridge 40 of FIG. 3. The base 42 has a central opening into which a stopper 50 is inserted. The hollow spike 41 can penetrate into the stopper and bore through its base 51 and thus penetrate into the interior of the cartridge 40. Further, a plurality of rings 52 are formed thereon; their floors 53 are also sealed. One of the floors 53 of the rings 52 may, for example, be pierced by the spike 32 acting as an electrode.

Figure 5:
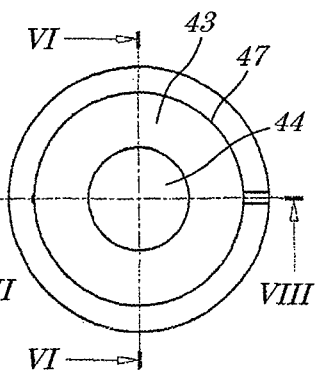
FIG. 5 shows a top view of the cartridge of FIG. 3.

FIG. 5 shows a top view of the cartridge 40 of FIG. 3. It can be seen that the top 43 of the upper part 47 of the cartridge 40 is formed as a ring which borders the depression 44 into which the guide spike 38 of the mounting 21 of the aerosol generator 20 can penetrate. The hollow spikes 39 of the mounting 21 are preferably disposed such that when the spikes penetrate into the top 43, evenly distributed openings in the ring 43 are introduced into the top of the cartridge 40.

Figure 6:
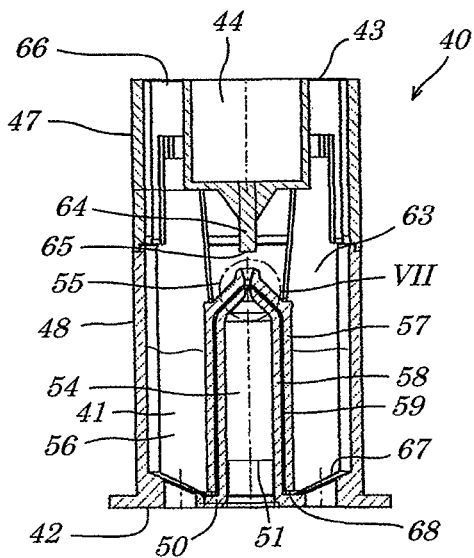
FIG. 6 shows a longitudinal axial section through the cartridge of FIG. 3 along the line VI-VI of FIG. 5.
Figure 7:
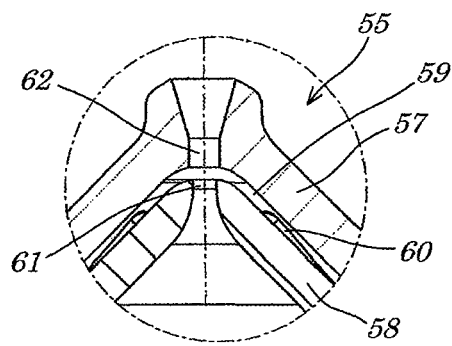
FIG. 7 shows a detailed enlargement of the section of FIG. 6.

FIG. 6 shows a longitudinal section of the cartridge 40 of FIG. 3 along the plane defined by line VI-VI of FIG. 5. It can be seen that the cartridge has a central bore 54 which extends from the base 51 of the central ring 50 and leads into a nozzle tip 55. FIG. 7 is an enlarged view of the nozzle tip 55 circled at VII in FIG. 6.

The bore 54 acts as a supply line for the carrier gas which is blown into the nozzle 55. The nozzle tip 55 is formed as a Venturi nozzle so that the carrier gas passing through the nozzle can draw in the fluid to be atomized from a reservoir 56 of the cartridge 40. The nozzle 55 consists of an outer shell 57 which in the present case is formed together with the lower part 48 as a single injection molded part. An inner shell 58 representing a separate injection molded part is inserted through the base 42 of the cartridge into the outer shell when manufacturing the cartridge such that an annular channel 59 is left between the inner shell and the outer shell which communicates with the reservoir 56 and via which the fluid 41 to be atomized can be drawn into the nozzle tip 55. To keep the annular channel 59 open even when the central bore 54 is pressurized, a plurality of ribs 60 may be provided on the top side of the inner shell 58 or on the underside of the outer shell 57 to act as spacers (see FIG. 7 in particular). The carrier gas flowing out from the opening 61 of the inner shell 58 through the opening 62 of the outer shell 57 results in an underpressure in the annular gap 59 which draws the fluid to be atomized out of the reservoir 56 towards the opening 62. The angle of the opening 62 of the outer shell 57 in the example shown is approximately 32°. The diameter of the opening 61 in the example of FIGS. 3 to 9 is approximately 0.6 mm and the diameter of the opening 62 at the narrowest point is 0.9 mm. If the supply line 54 is pressurized with a carrier gas pressure of approximately 2 bar, fluid particles in the sub-micrometer range and fluid particles with diameters of more than 1 μm are produced on leaving the nozzle tip 55. In order to separate the larger from the smaller fluid particles, a demixing chamber 63 is provided in the cartridge in the transitional region between the upper part 47 and the lower part 48. The demixing chamber 43 comprises a deflection device 64, which has a die 65 which in the assembled condition of the cartridge is positioned approximately 2 mm above the nozzle opening 62. Within the limits of the set angle of the nozzle opening 62, the mixture of larger and smaller fluid particles leaving the nozzle 62 is expelled essentially axially upwards out of the nozzle 62 and impinges immediately directly on the deflection device 64. The fluid particles are thus deflected sideways so that larger fluid particles can flow under gravity back into the fluid reservoir 56, while smaller fluid particles in the sub-micrometer range are carried out through openings 66 which are formed by the spikes 39 of the mounting 21 in the top 43 of the cartridge 40. With the cartridge according to the invention, it can thus be ensured that the fluid 41 in the cartridge is essentially dispensed completely in the form of a nanoaerosol into the environment. In order to be able to use up the last drops of fluid, the base 67 of the fluid reservoir 56 is inclined towards the gap 68 at the bottom of the channel 59.

Figure 8:
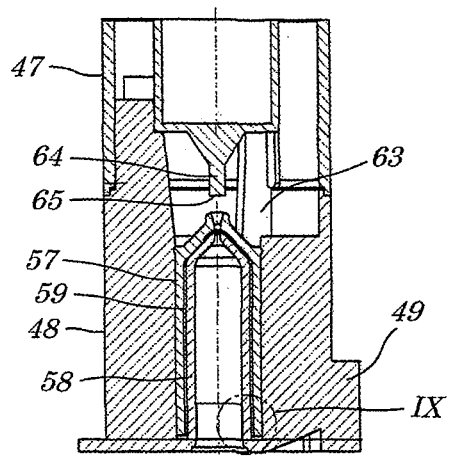
FIG. 8 shows a longitudinal axial section of the cartridge of FIG. 3 along the line VIII-VIII in FIG. 5.

FIG. 8 shows a longitudinal section of the cartridge 40 of FIG. 3 in the plane defined by the line VIII-VIII. Inwardly directed ribs to reinforce the cartridge lie in this plane.

Figure 9:
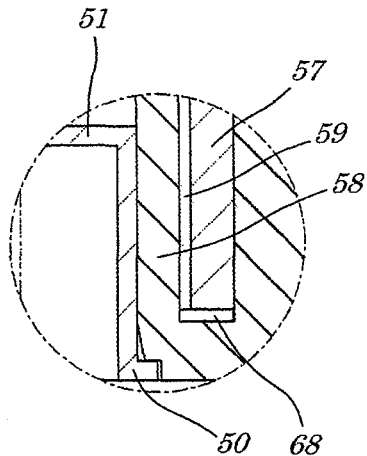
FIG. 9 shows an enlarged detailed view of the section of FIG. 8.

FIG. 9 shows the bottom region of the inner shell 58 and outer shell 57 enclosed in the circle in FIG. 8 with the gap 68 formed at the bottom of the channel 59 formed between the inner shell and the outer shell shown in more detail.

Figure 10:
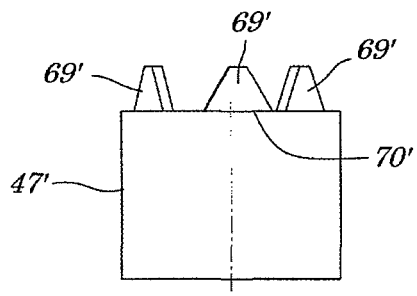
FIG. 10 shows a variant of the upper part of the cartridge of FIG. 3.

FIG. 10 shows a variant 47' of the upper part 47 of the cartridge 40 in FIG. 3. In this case, the upper part 47' has tear tabs 69' on its top 43' which are formed as one piece with the upper part 47'. When the tear tabs 69' are snapped off, they expose openings in their bottom region 70' formed in the top 43' of the upper part 47', through which the nanoaerosol can escape from the cartridge. In order to guarantee snapping off of the tear tabs 69', the upper part 22 of the mounting 21 of FIG. 2 has no spikes 39 but may, for example, have a slightly tapered inner surface which pushes the tear tabs inwards when the pneumatic drive 24 pushes the cartridge into the upper part 22 via the movable lower part 23 of the mounting 21. Thus, the upper part 22 of the mounting is particularly easy to clean.

Figure 11:
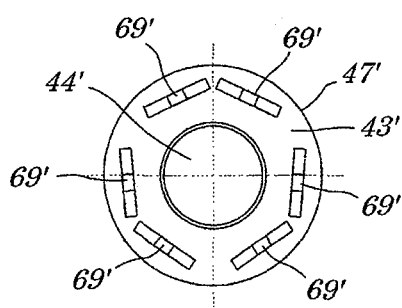
FIG. 11 shows a top view of the variant of the upper part of FIG. 10.

FIG. 11 shows a top view of the upper part 47' of FIG. 10.

Figure 12:
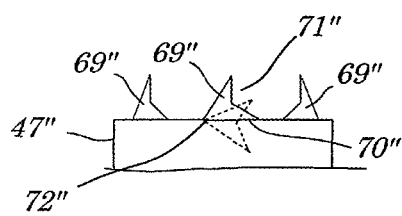
FIG. 12 shows a first variant of the tear tab of FIG. 10.

FIG. 12 shows a variant 69'' of the tear tabs 69' of FIG. 10. In the example shown, the tear tabs 69'' differ from the triangular tear tabs 69' of FIG. 10 in that they have a recess 71'' at one side. In order to form an opening 70'' in the top of the upper part 47'' of FIG. 12, the tear tabs 69'' are not bent inwards, but are pushed downwards in the plane of FIG. 12. The tear tabs 69'' thus essentially turn about a corner point 72'' into the configuration of the tear tab shown in dashed lines in FIG. 12, whereupon an opening 70'' in the surface 43'' is exposed.

Figure 13:
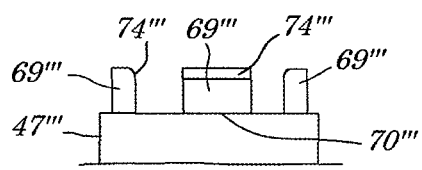
FIG. 13 shows a second variant of the tear tab of FIG. 10.

FIG. 13 shows a further variant 69''' of the tear tab 69''' of FIG. 10. The tear tab 69''' of FIG. 13 is essentially rectangular and has a rounded upper edge 74'''. Thus, the upper part 22 of the mounting 21 (FIG. 2) can be formed as a hollow cylinder, making cleaning thereof even simpler.

Figure 14:
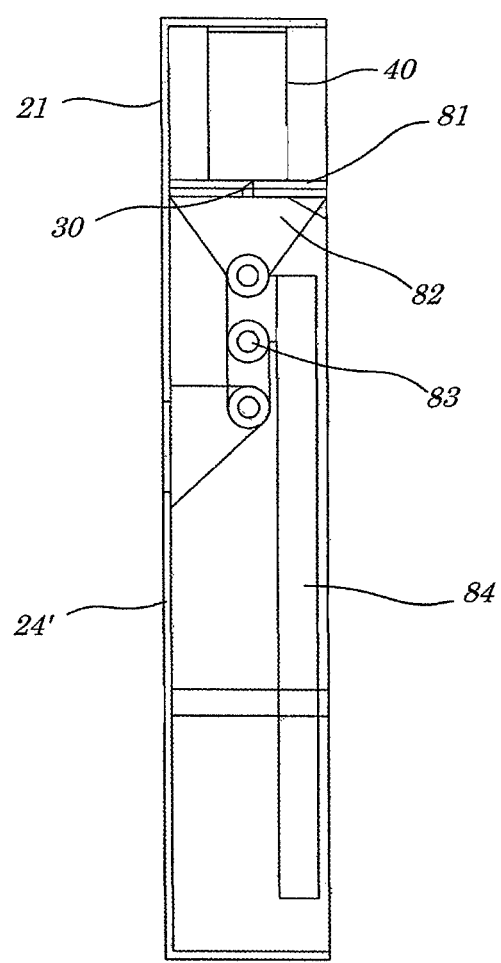
FIG. 14 shows a variant of the drive for the cartridge housing of FIG. 2.

Finally, FIG. 14 diagrammatically shows a less expensive variant 24''' of the cartridge drive 24 of the aerosol generator of FIG. 2. The aerosol generator essentially corresponds to the aerosol generator 20 of FIG. 2; for the sake of clarity, therefore, not all of its components are shown. The aerosol generator again has a mounting 21 for a replaceable cartridge 40 which contains the fluid to be atomized. Instead of a pneumatic drive (reference numeral 24 in FIG. 2) to drive the spikes into the cartridge, in the variant of FIG. 14, a purely mechanical drive 24' is provided. The cartridge 40 is placed on an upper cradle 81 which is movably mounted in the mounting 21. The central hollow spike 30 described in FIG. 2 is positioned on a movable lower cradle 82. In the example shown, the lower cradle 82 is moved upwards by means of a manually actuatable toggle lever 83 so that on the one hand the spike 30 is stabbed into the base of the cartridge 40 and on the other hand the upper cradle 81 with the cartridge 40 is forced against the upper part 22 (not shown in FIG. 14) of the mounting. To this end, the toggle lever 83 has an actuating arm 84 that can be operated by the user. The upper part 22, not shown, has spikes the form of which depend on the embodiment of the cartridge 40 to produce the discharge openings in the cartridge (comparable to the spikes 38 in FIG. 2) or only an appropriate counter ring to snap off the tear tabs of the cartridge 40. The compressor 25 (not shown in FIG. 14) is then no longer responsible for the drive, but only for generating compressed air which is blown through the hollow spike 30 into the cartridge 40. Clearly, in this variant, an electrode (not shown here but analogous to electrode 32 in FIG. 2) may be inserted into the cartridge in order to charge the fluid electrostatically.

The invention claimed is:

1. A cartridge for generating a nanoaerosol, the cartridge comprising:
   at least one reservoir for the fluid to be atomized,
   a demixing chamber which comprises a deflection device and at least one discharge opening for the fluid to be atomized,
   a nozzle which has at least one nozzle opening leading into the demixing chamber; and
   at least one channel from the reservoir which opens into the nozzle, wherein the cartridge includes an element for enabling a connection with an electrical voltage supply source.

2. The cartridge as claimed in claim 1, wherein a communicating connection is provided between the reservoir and the demixing chamber.

3. The cartridge as claimed in claim 1, wherein at least one supply line for a carrier gas is provided which leads into the nozzle.

4. The cartridge as claimed in claim 3, wherein the supply line for the carrier gas is formed as a central bore one end of which joins the base of the cartridge and the other end of which merges into the nozzle.

5. The cartridge as claimed in claim 4, wherein the bore which joins the base of the cartridge is sealed by a pierceable wall.

6. The cartridge as claimed in claim 1, wherein the at least one discharge opening for the fluid to be atomized is sealed by a pierceable or tear-open wall.

7. The cartridge as claimed in claim 1, wherein the nozzle is formed as a Venturi nozzle.

8. The cartridge as claimed in claim 1, wherein the cartridge comprises
   at least two components which can be connected together after filling with the fluid to be atomized, wherein the at least two components are connected together in a non-detachable manner.

9. The cartridge as claimed in claim 1, wherein the reservoir contains a fluid to be atomized.

10. An aerosol generator, comprising:
    a mounting to accommodate at least one cartridge including at least one reservoir containing a fluid to be atomized and means for expelling the fluid contained in the at least one cartridge,
    a demixing chamber which comprises a deflection device and at least one discharge opening for the fluid to be atomized,
    a nozzle which has at least one nozzle opening leading into the demixing chamber;
    at least one channel from the at least one reservoir which opens into the nozzle; and
    an electrical voltage supply source coupled to an element supported by the mounting.

11. The aerosol generator as claimed in claim 10, wherein the means for expelling the fluid contained in the cartridge comprise
    a source of a carrier gas, wherein the mounting has at least one first hollow spike which communicates with the source of a carrier gas and which can penetrate into the cartridge's supply line for the carrier gas, and
    at least one second hollow spike which communicates with the environment and which can penetrate into the cartridge's discharge opening for the fluid to be atomized.

12. The aerosol generator as claimed in claim 11, wherein the source of a carrier gas comprises a compressor or a compressed gas bottle containing an inert gas.

13. The cartridge as claimed in claim 1, wherein the element is a first penetrable barrier arranged along a first surface of the cartridge.

14. The cartridge as claimed in claim 13, wherein the first penetrable barrier is pierced by a conductor coupled to the electrical voltage supply.

15. The cartridge as claimed in claim 14, wherein the first penetrable barrier is further pierced by a hollow spike coupled to a source of compressed air.

16. The cartridge as claimed in claim 13, wherein the element is a second penetrable barrier arranged along a second surface of the cartridge.

17. The cartridge as claimed in claim 16, wherein the first surface is opposed to the second surface.

18. The cartridge as claimed in claim 16, wherein the second penetrable barrier is pierced by a hollow spike coupled to the electrical voltage supply.

19. The aerosol generator of claim 10, wherein the element supports at least one hollow penetrating member.

20. The aerosol generator of claim 19, further comprising:
    a drive that compresses the cartridge between the element supported by the mounting and a conductor coupled to the electrical voltage supply to pierce the at least one reservoir.

* * * * *